United States Patent [19]

Rydell

[11] Patent Number: 5,035,696
[45] Date of Patent: Jul. 30, 1991

[54] ELECTROSURGICAL INSTRUMENT FOR CONDUCTING ENDOSCOPIC RETROGRADE SPHINCTEROTOMY

[75] Inventor: Mark A. Rydell, Golden Valley, Minn.

[73] Assignee: Everest Medical Corporation, Minneapolis, Minn.

[21] Appl. No.: 474,481

[22] Filed: Feb. 2, 1990

[51] Int. Cl.⁵ .............................................. A61B 17/39
[52] U.S. Cl. ........................................ 606/47; 606/48
[58] Field of Search ............................. 606/47, 48, 50

[56] References Cited

U.S. PATENT DOCUMENTS

| 4,311,143 | 1/1982 | Komiya | 606/47 |
|---|---|---|---|
| 4,325,374 | 4/1982 | Komiya | 606/47 |
| 4,493,320 | 1/1985 | Treat | 606/47 |
| 4,846,175 | 7/1989 | Frimberger | 606/47 |

FOREIGN PATENT DOCUMENTS 2426781 12/1975 Fed. Rep. of Germany ........ 606/47

Primary Examiner—Lee S. Cohen
Attorney, Agent, or Firm—Haugen and Nikolai

[57] ABSTRACT

A bioplar sphinctertome for use in endoscopic retrograde sphincterotomy procedures includes an elongated, flexible, plastic tube having either a single or a double lumen and includes a segment near its distal end which is both flexible and conductive. This segment is connected by a wire extending through the lumen to a terminal at the proximal end of the device adapted to be coupled to an electrosurgical generator. A second, longitudinally movable wire passes through the lumen and is connected at the proximal end to a finger-operated slide mechanism while its distal end passes through a small aperture formed in the tube just proximal of the flexible conductive segment. That wire is then anchored distally of the flexible conductive segment so that when a tensioning force is applied to the wire, the distal end portion of the instrument will bow, with the exposed wire comprising the active electrode and the flexible conductive segment functioning as the return electrode. A two-piece handle assembly permits the sphinctertome to be treated as a disposable, single-use surgical instrument.

13 Claims, 2 Drawing Sheets

U.S. Patent     July 30, 1991     Sheet 1 of 2     5,035,696
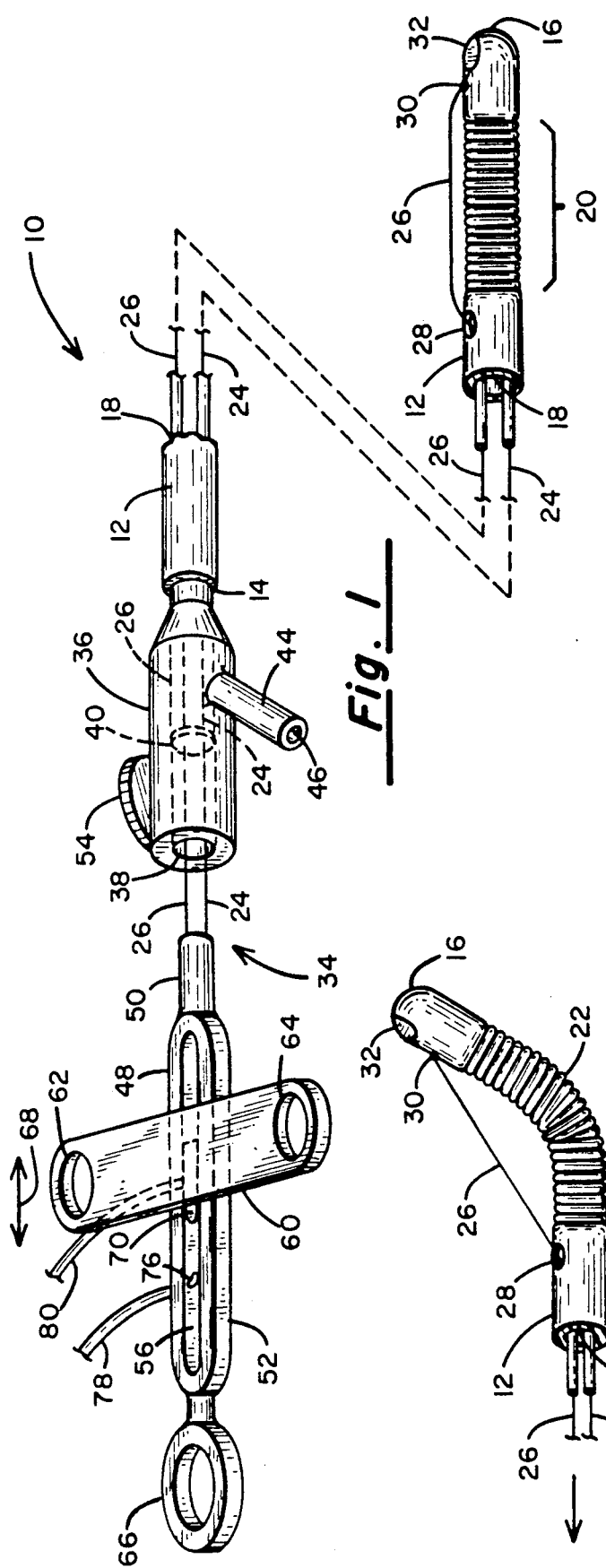
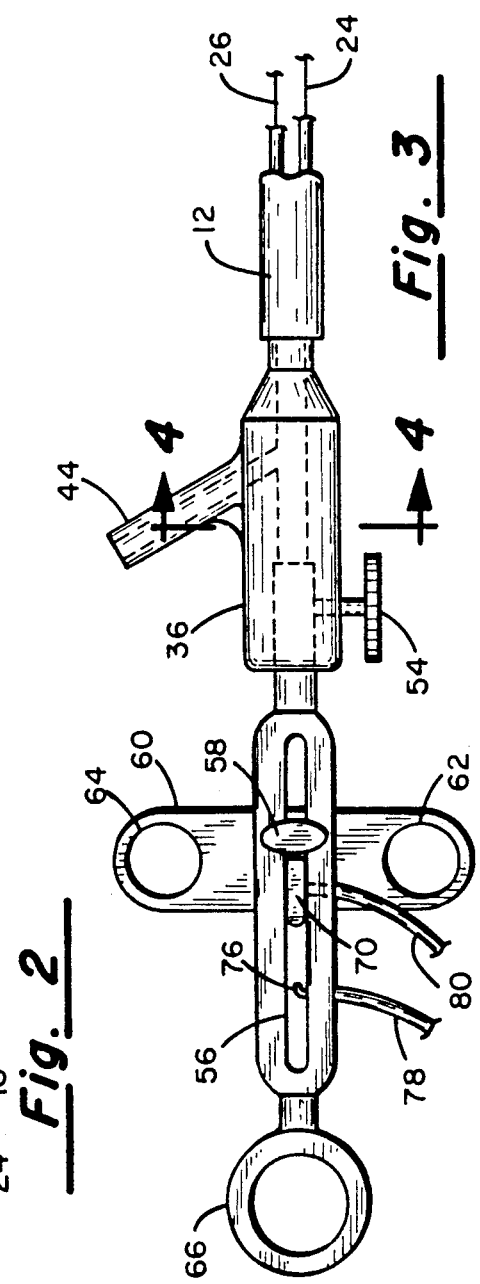

ELECTROSURGICAL INSTRUMENT FOR CONDUCTING ENDOSCOPIC RETROGRADE SPHINCTEROTOMY

BACKGROUND OF THE INVENTION

I. Field of the Invention

This invention relates generally to electrosurgical apparatus, and more particularly to a catheter-based, bipolar electrosurgical device which can be passed through an endoscope into the duodenum to the site of the papilla of Vater and which can be deployed to cut the sphincter of Oddi to allow passage of gallstones from the common bile duct into the duodenum.

II. Discussion of the Prior Art

When gallstones form in the gallbladder and achieve a size too large to pass through the cystic duct and the common bile duct into the duodenum, a gallbladder attack may result leading to intense pain and possible surgical removal of the gallbladder itself. Where the site of the blockage is the sphincter of Oddi, a less traumatic procedure referred to as "endoscopic retrograde sphincterotomy" (ERS) may be used to cut the sphincter sufficiently to permit even large size gallstones to pass into the duodenum. In carrying out the ERS procedure, a side-viewing endoscope is passed through the esophagus into the stomach and from there through the pyloric sphincter into the duodenum. Using a fiber optic bundle, the distal end of the endoscope is made to approach the papilla of Vater and, when so positioned, a cannula is passed through the endoscope and through the sphincter of Oddi into the common bile duct. At this point, a contrast fluid may be injected so that any gallstones can be viewed fluoroscopically and their size evaluated. If a stone is deemed to be too large to pass through the sphincter of Oddi even when enlarged, the sphincterotomy procedure is terminated and the patient at that point becomes an abdominal surgery candidate. However, if the size of the gallstones are sufficiently small, an electrosurgical instrument referred to as a sphinctertome or papillatome is made to pass through a side port in the endoscope and through the sphincter of Oddi. At this point, the instrument is used to cut the sphincter of Oddi to effectively allow it to expand and pass gallstones of a size too large to pass through that sphincter normally.

Electrosurgical sphinctertomes of the prior art have been monopolar in nature. In particular, it would typically comprise an elongated tube having a proximal end, a distal end and a lumen extending between the two ends. A small aperture is formed a short distance proximal of the distal end and a conductive wire is routed through the lumen of the tube, out the aperture and then anchored proximate the distal tip of the tube. This wire would be electrically coupled to an electrosurgical generator whose other terminal connects to an indifferent electrode called a patient plate placed in electrical contact with the patient's buttocks. By applying a tension force to the proximal end of the aforementioned wire following its placement through the sphincter of Oddi, the tip portion of the sphinctertome becomes bowed and when the voltage is applied between the wire and the patient plate, a current flows from the wire through contacting tissue and from there through a path of least resistance to the patient plate.

The use of a monopolar sphinctertome has led to a number of problems, chiefly due to the unpredictable nature of the current return path through the body to the patient plate. Where conductive fluids have been introduced into the common bile duct at the outset to assess stone sizes, that fluid also finds its way into the pancreatic duct which is directly adjacent the sphincter of Oddi. Recognizing that the contrast fluid is a highly conductive liquid, one path of least resistance from the monopolar cutting wire to the patient plate is through pancreatic tissue. This current flow has been found to raise the temperature of the pancreas to the point where cells become inflamed, leading to a serious condition called "pancreatitis". It is also found the depth of tissue destruction resulting from a monopolar electrosurgical sphinctertome may be excessive and in some instances, this has led to a perforation of the bowel. In this event, the patient must undergo abdominal surgery to correct that condition.

In that the site of the sphincter of Oddi is highly vascularized, considerable bleeding takes place during a ERS procedure, especially where a monopolar electrosurgical sphinctertome is employed.

SUMMARY OF THE INVENTION

Most of the foregoing problems are obviated through the use of the sphinctertome of the present invention. Rather than being monopolar in nature, the present invention comprises a bipolar sphinctertome.

The device itself has an elongated flexible tubular catheter body with a proximal end, a distal end and at least one lumen extending the length of the catheter. Near the distal end of the catheter tube is disposed a flexible conductive segment normally coaxially aligned with the tube. Just proximal of this flexible conductive segment is an aperture which extends through the side wall of the tube. Passing through the lumen from the proximal end are first and second conductors, one being electrically joined to the flexible conductive segment and the other passing from the lumen through the aperture to the exterior and thence parallel to the flexible conductive segment to an anchoring point at the distal end portion of the catheter body.

Located at the proximal end of the tubular catheter is a handle member having a finger-operated slide coupled to the conductor whose distal end portion passes through the aperture in the catheter body. By manipulating the slide, the distal end portion of the catheter may be made to bow. The flexible conductive segment and the length of wire extending parallel thereto form a bipolar electrode pair. When the distal end portion of the catheter is fitted through the sphincter of Oddi and a high frequency voltage is applied across the two conductors, the resulting current path is localized to the tissue present between the active wire electrode and the flexible conductive segment which comprises the return electrode.

. The use of the bipolar sphinctertome of the present invention allows better control over the depth of tissue destruction which is much less than is the case when a monopolar sphinctertome is employed. Also, since the current path is concentrated to the area of the surgery, greatly improved hemostasis can be achieved. Moreover, incidences of pancreatitis occasioned by errant currents seeking a return to the patient plate is obviated.

As will be set out in greater detail hereinbelow, a further advantage of the bipolar sphinctertome of the present invention resides in the fact that the area of the flexible conductive segment and that of the active wire electrode which extends parallel to it in passing into the sphincter of Oddi, remains substantially constant. As such, better control can be maintained over the power level delivered to the site of the surgery.

DESCRIPTION OF THE DRAWINGS

The foregoing objects, features and advantages of the invention will become more apparent to those skilled in the art from the following detailed description of various embodiments of the invention in which like numerals in the several views refer to corresponding parts.

FIG. 1 is a perspective view of the sphinctertome apparatus of the present invention;

FIG. 2 is a partial view of the apparatus of FIG. 1 showing the distal portion of the bipolar sphinctertome in its cutting position;

FIG. 3 is a bottom plan view of the handle portion of the sphinctertome device of FIG. 1;

DESCRIPTION OF THE PREFERRED EMBODIMENTS

Figure 6:
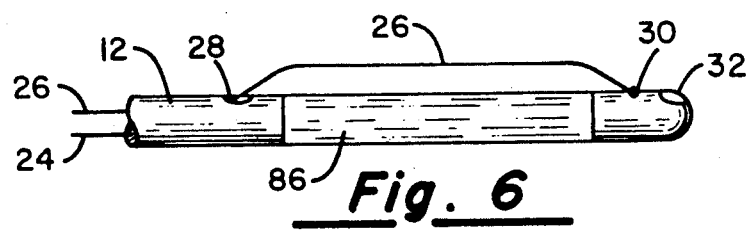
FIG. 6 is a fragmentary view of the distal end portion of the sphinctertome device in accordance with an alternative embodiment.

Referring first to FIG. 1, there is indicated generally by numeral 10 a sphinctertome to be used during an endoscopic retrograde sphincterotomy to enlarge the opening surrounded by the sphincter of Oddi so that gallstones of a predetermined size or less may more readily pass from the common bile duct into the duodenum. It is seen to comprise an elongated flexible tubular member 12 having a proximal end 14 and a distal end 16 with at least one lumen 18 extending between the proximal end distal ends. Coaxially disposed a short distance proximal of the distal end 16 of the tube 18 is a flexible conductive segment shown enclosed by brackets 20. In the embodiment of FIG. 1, the flexible conductive segment 20 comprises a helically wound wire spring 22 to which an electrical conductor 24 connects, that conductor extending back through the lumen 18 to the proximal end of the tube 12 and there beyond. Also extending through the lumen 18 and insulated from the conductor 24 is a stainless steel wire 25 having an outside diameter of about 0.012 inch. The wire 26 exits the tube 12 via a small lateral aperture 28 formed through the wall of the tube and then extends generally parallel to the flexible conductive segment 20 until being mechanically attached at point 30 to the wall of the plastic tube 12. A further aperture or port 32 extends through the wall of the tube 12 at its distal end 16 allowing a flushing liquid or a contrast liquid to be injected into the body proximate the surgical site if desired.

Figure 4:
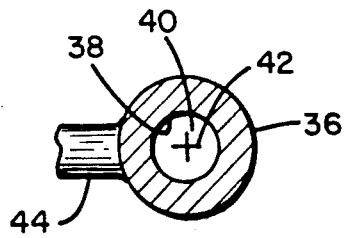
FIG. 4 is a cross-sectional view taken along the line 4—4 in FIG. 3.

Coupled to the proximal end 14 of the elongated plastic tubular catheter body 12 is a two-piece handle segment, indicated generally by numeral 34. The forward or more distal segment of the two-piece handle is identified by numeral 36 and is seen to be generally tubular in form, having a central bore 38 extending the length thereof. Positioned within the bore 38 is a flexible, elastomeric disk 40 positioned transverse to the longitudinal axis of the bore 38. Formed centrally in the disk 40 is a cruciform self-sealing slit 42 (FIG. 4) which permits the conductors 24 and 26 to pass therethrough but which forms a liquid-tight seal thereabout.

Projecting laterally from the handle segment 36 and integrally molded therewith is a tubular stem 44 having an internal Luer fitting 46 formed on the end thereof whereby the tubular stem 44 may be connected to a syringe or other source of a flushing or contrast liquid (not shown). The lumen of the stem 44 intersects with the bore 38 of the handle portion 36 and that bore, in turn, is in fluid communication with the lumen 18 of the elongated flexible plastic tubular member 12. As such, a liquid introduced through the port 46 may be made to flow through the tube 12 and out its distal ejection port 32.

The second segment of the two-piece handle is identified by numeral 48 and may be generally cylindrical in form having a distal nose portion 50 of a reduced diameter as compared to its main body portion 52. Member 48, like segment 36, may preferably be formed in a plastic molding operation from any one of a number of medical grade plastics. The nose portion 50 is adapted to be inserted into the bore 38 of the handle segment 36 and when so inserted, may be held in place by a set screw (not shown) which fits into a threaded bore extending transverse to the bore 38. The set screw is provided with a thumb wheel 54 to facilitate its loosening and tightening.

Formed through the cylindrical body of the handle segment 48 is a longitudinal slot 56. With reference to the bottom view of FIG. 3, it can be seen that a pin with an enlarged head 58 passes transversely through the slot 56 and into a slide member 60 having finger holes 62 and 64 formed therethrough. A thumb-receiving ring 66 is integrally molded with or otherwise affixed to the body member 52 allowing the surgeon to readily grasp the handle portion and manipulate the slide plate 60 in the proximal or distal direction as indicated by the doubled-headed arrow 68 by inserting the forefinger and the index fingers through the openings 62 and 64.

The conductor 26 has a cylindrical, conductive contact 70 attached to its proximal end which is fitted into a recess formed on the underside of the slide 60 such that the wire 26 will move axially with the slide plate 60. An electrical connector pin 72 passes through the side wall of the cylindrical member 52 and into the slot 56. A wire or cable 78 connects to that connector ping 76 to a terminal of an electrosurgical generator (not shown). The conductor 24 also connects to a contact also passing through the wall of the slot 56 and a conductor 80 joins thereto and leads to the other output terminal of the electrosurgical generator. An electrosurgical generator suitable for use with the sphinctertome of the present invention may be that described in the Stasz et al patent application Ser. No. 07/254,203, allowed Oct. 6, 1989, and entitled "Electrosurgical Generator" and assigned to the assignee of the present invention.

FIG. 2 is an illustration of the distal end portion of the sphinctertome of FIG. 1 when the slide plate 60 is pulled in the proximal direction to apply a tension force on the conductor 26. The conductive segment 22 of the device being flexible, allows the instrument to bow in the manner shown. When the slide 60 is pulled proximally to the point where the conductive contact 70 on the end of the conductor 26 abuts the contact 76, an RF voltage from the generator can be applied when the surgeon depresses a foot switch (not shown) current flow between the cutting wire 26 and the flexible conductive return electrode 20 effects cutting of cell tissue present between the cutting wire 26 and the indifferent electrode.

Figure 5:
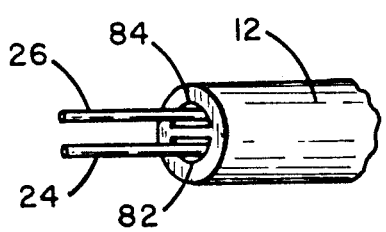
FIG. 5 is a fragmentary view of portion of the tubular catheter utilizing a bilumen construction.

FIG. 5 illustrates an arrangement where the elongated flexible plastic tube 12 includes a pair of lumens 82 and 84 for maintaining the wires 24 and 26 insulated from one another along their length. In this arrangement, the conductors 24 and 26 may comprises bare wires whereas in the arrangement shown in FIGS. 1 and 2 involving a single lumen tube, the wires 24 and 26 must be coated with an insulating layer to prevent short circuiting. Flushing liquid is introduced only into the lumen to which aperture 32 joins.

FIG. 6 illustrates an alternative arrangement where the flexible conductive segment 20 located near the distal end of the tubular body 12 comprises a conductive coating 86 on the exterior of tube 12 rather than a helically wound wire spring element like member 22 in FIG. 1.

Figure 7:
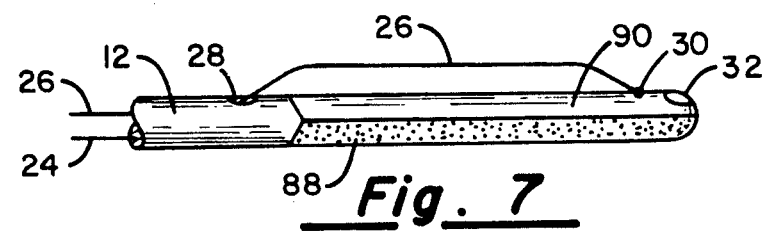
FIG. 7 is a fragmentary view of the distal end portion of the sphinctertome device in accordance with yet another alternative embodiment.

In the alternative embodiment of FIG. 7, the distal end portion is formed of a composite of a conductive silicone layer 88 bonded to a non-conductive silicone layer 90, the conductor 24 being electrically joined to the conductive silicone layer 88 internal to the catheter body.

Figure 8:
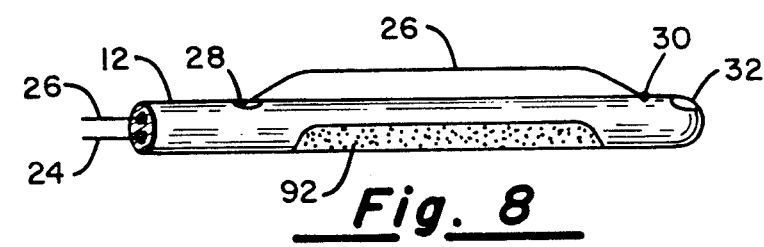
FIG. 8 is a fragmentary view of the distal end portion of the sphinctertome device in accordance with a yet further embodiment.

FIG. 8 is still another alternative arrangement in which a bilumen tube 12 is employed with one of the lumens being filled with a conductive polymer at its distal end to function as the return electrode as at 92. The side wall of the tube 12 is then ground away to expose the conductive polymer.

Figure 9:
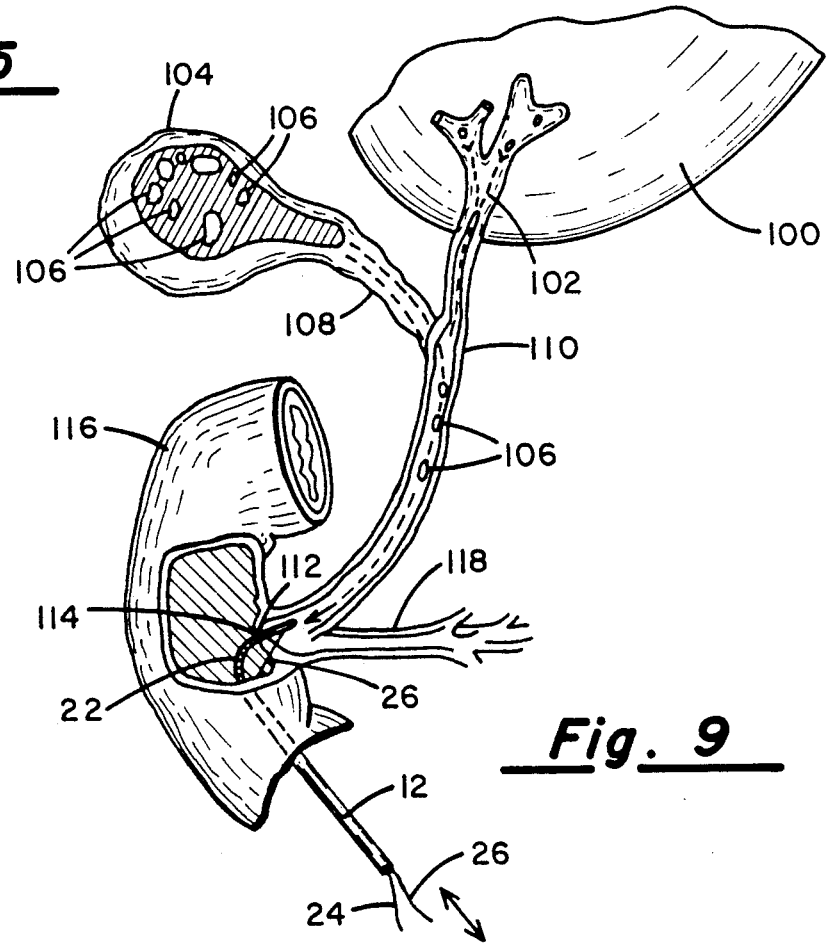
FIG. 9 is an anatomical diagram of the accessory organs of the digestive tract helpful in illustrating the use of the sphinctertome of the present invention.

Having described the various embodiments of the sphinctertome comprising the present invention, attention will next be given to its mode of use and, in that regard, reference will also be had to the anatomical diagram illustrated in FIG. 9. In this diagram, the liver is identified by numeral 100 and the hepatic duct by numeral 102. The gallbladder is identified by numeral 104 and is sectioned to reveal a number of gallstones as at 106, the stones varying in both size and shape. The cystic duct 108 connects the gallbladder 104 to the common bile duct, which is also sectioned open to reveal the presence of further stones 106 therein.

The common bile duct leads to the sphincter of Oddi 112 located at the duodenal papilla 114 sometimes referred to as the papilla Vater. The duodenum is identified by numeral 116 and the pancreatic duct by numeral 118.

When gallstones form because of an excess of cholesterol in the bile and/or the absorption of too much bile acids from the bile, they may pass from the gallbladder and down the common bile duct into the duodenum without problem provided the stones are sufficiently small. Occasionally, however, the gallstones within the gallbladder develop to a size where they may block the normal flow of bile during digestion of fatty foods, resulting in a blockage of the cystic duct 108 or the common bile duct 110. The sphincter of Oddi comprises a restriction and is a location where a larger stone may not be able to pass. In the ERS procedure, a side viewing endoscope is inserted down the patient's esophagus through the stomach and into the duodenum. While viewing the surgical site through a fiber optic rod, the surgeon may first pass a small diameter cannula through a side port of the endoscope to gently lift the tissue flap covering the papilla of Vater at 114 and then it is advanced into the common bile duct. A suitable contrast fluid, such as Hypaque ® meglumine 60%, may then be injected through the cannula whereby the condition of the common bile duct and the stone content thereof can be assessed. Subsequently, the elongated tube portion 12 of the sphinctertome 10 is routed through the endoscope and the rounded distal tip 16 is advanced through the sphincter. (In FIG. 9, the endoscope is not shown so that the sphinctertome of the present invention can better be viewed.) At this time, the tension on the cutting wire 26 is nil and the distal end portion of the sphinctertome remains relatively straight. With the distal end portion of the sphinctertome so positioned, the surgeon may next pull back in the proximal direction on the slide bar 60 and, in doing so, will apply a tensioning force to the cutting wire 26 causing the distal end portion to bow as illustrated in FIG. 2. When the point is reached that the contact 70 engages the contact 76 and the foot switch is depressed, the RF voltage provided by the electrosurgical generator is applied between the cutting wire 26 to the flexible conductive segment 20 which forms a bipolar electrode pair. In that the tissue comprising the sphincter of Oddi will at this time be in contact with the wire 26 and the return electrode, the tissue will be cut at its point of contact with the wire 26 to thereby enlarge the opening defined by the sphincter of Oddi. At this point, substantially larger stones than could normally pass will find their way out through the enlarged sphincter into the duodenum and will then pass through the remainder of the digestive tract.

By utilizing an appropriate power setting on the electrosurgical generator, e.g., the blend mode discussed in the aforereferenced Stasz et al patent application, the cutting is accompanied by coagulation, thereby significantly reducing the loss of blood. Moreover, because the electrode configuration is bipolar, the current path is only through tissue abutting the cutting wire 26 and the return electrode 22. Hence, the tendency for substantial electrical currents to flow through the conductive contrast fluid or other body fluids contained in the pancreatic duct is eliminated and the likelihood of a subsequent inflammation of the pancreas often accompanying monopolar sphincterotomy is markedly reduced.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A bipolar electrosurgical instrument for performing a sphincterotomy comprising:
    (a) an elongated flexible plastic tubular member of a predetermined diameter having a proximal end, a distal end and at least one lumen extending between said proximal end and said distal end, said tubular member including an aperture extending through its wall into said lumen at a location proximate said distal end;

(b) a flexible conductive member with first and second ends and an outer diameter generally equal to said predetermined diameter coaxially affixed at said first end to said distal end of said plastic tubular member;

(c) first conductor means extending through said lumen from said proximal end to said distal end and electrically coupled to said flexible conductive member to create a return electrode; and (d) second conductor means extending through said lumen from said proximal end, out through said aperture and parallel to said flexible conductive member and insulatively coupled to said second end of said flexible conductive member with said first and second conductor means insulated from one another along the length of said lumen, said second conductor means being uninsulated over the parallel extending portions of said flexible conductive member and said second conductor means to form an active electrode, said second conductor means being free to move longitudinally within said lumen to bow said flexible conductive member when a pulling force is applied to said second conductor means at said proximal end of said tubular member.

2. The electrosurgical instrument as in claim 1 and further including means for coupling a high frequency voltage source across said first and second conductor means at said proximal end of said tubular member.

3. The electrosurgical instrument as in claim 2 and further including plastic handle means attached to said proximal end of said tubular member, said handle means including a longitudinally movable slide member coupled to said second conductor means for applying said pulling force.

4. The electrosurgical instrument as in claim 3 wherein said handle means further includes first and second electrical connectors for coupling said first and second conductor means to said voltage source.

5. The electrosurgical instrument as in claim 3 and further including means in said handle means for introducing one of a contrast and flushing liquid into said lumen.

6. The electrosurgical instrument as in claim 1 wherein said second conductor means is a multifilar cable.

7. The electrosurgical instrument as in claim 1 wherein said tubular member includes two lumens separately containing said first and second conductor means.

8. The electrosurgical instrument as in any one of claims 1 through 7 wherein said flexible conductive member is a helically wound conductive wire spring.

9. The electrosurgical instrument as in any one of claims 1 through 7 wherein said flexible conductive member comprises a flexible plastic tube segment having a metallized coating thereon.

10. The electrosurgical instrument as in any one of claims 1 through 7 wherein said flexible conductive member comprises a conductive polymer.

11. The electrosurgical instrument as in claim 4 wherein one of said first and second electrical connectors includes contacts which close to complete a circuit to said voltage source only when said pulling force is being applied.

12. The electrosurgical instrument as in claim 5 wherein said flexible conductive member is tubular and includes a lumen in fluid communication with said lumen of said elongated flexible plastic tubular member.

13. The electrosurgical instrument as in claim 3 wherein said handle means comprises first and second separable segments, one segment being affixed to said proximal end of said tubular member and the segment including said slide member being separable from the segment to which said tubular member is affixed.

* * * * *